(12) United States Patent
Coe et al.

(10) Patent No.: US 6,324,434 B2
(45) Date of Patent: Nov. 27, 2001

(54) LEAD LOCKING DEVICE AND METHOD

(75) Inventors: Michael Sean Coe, Colorado Springs; Kenneth D. Harlan, Peyton, both of CO (US); Cesar Diaz, Santa Margarita, CA (US); Thomas E. Plasket, Colorado Springs, CO (US)

(73) Assignee: Spectranetics Corporation, Colorado Springs, CO (US)

( * ) Notice: Subject to any disclaimer, the term of this patent is extended or adjusted under 35 U.S.C. 154(b) by 0 days.

(21) Appl. No.: 09/727,509

(22) Filed: Dec. 4, 2000

Related U.S. Application Data

(62) Division of application No. 09/285,720, filed on Apr. 5, 1999, now Pat. No. 6,167,315.

(51) Int. Cl.$^7$ ................................................ A61B 17/50
(52) U.S. Cl. ................................ 607/119; 606/108
(58) Field of Search .............................. 607/116, 119, 607/122; 606/108

(56) References Cited

U.S. PATENT DOCUMENTS

| | | |
|---|---|---|
| 3,906,938 | 9/1975 | Fleischhacker . |
| 4,000,745 | 1/1977 | Goldberg . |
| 4,471,777 | 9/1984 | McCorkle, Jr. . |
| 4,498,482 | 2/1985 | Williams . |
| 4,541,681 | 9/1985 | Dorman et al. . |
| 4,574,800 | 3/1986 | Peers-Trevarton . |
| 4,576,162 | 3/1986 | McCorkle . |
| 4,582,056 | 4/1986 | McCorkle, Jr. . |
| 4,706,671 | 11/1987 | Weinrib . |
| 4,721,118 | 1/1988 | Harris . |
| 4,762,130 | 8/1988 | Fogarty et al. . |
| 4,791,939 | 12/1988 | Maillard . |
| 4,796,642 | 1/1989 | Harris . |
| 4,827,941 | 5/1989 | Taylor et al. . |
| 4,943,289 | 7/1990 | Goode et al. . |
| 4,988,347 | 1/1991 | Goode et al. . |
| 5,011,482 | 4/1991 | Goode et al. . |
| 5,013,310 | 5/1991 | Goode et al. . |
| 5,207,683 | 5/1993 | Goode et al. . |
| 5,231,996 | 8/1993 | Bardy et al. . |
| 5,423,806 | 6/1995 | Dale et al. . |
| 5,549,615 | 8/1996 | Hocheri et al. . |
| 5,556,424 | 9/1996 | Hocheri et al. . |
| 5,593,433 | 1/1997 | Spehr et al. . |
| 5,620,451 | 4/1997 | Rosborough . |
| 5,632,749 | 5/1997 | Goode et al. . |
| 5,697,936 | * 12/1997 | Shipko et al. .................. 606/108 |
| 6,136,005 | 10/2000 | Goode et al. . |

* cited by examiner

Primary Examiner—George R. Evanisko
(74) Attorney, Agent, or Firm—Pillsbury Winthrop LLP

(57) ABSTRACT

A lead locking device has a lead engaging member with a mandrel extending along a lumen and attached to the distal end of the lead engaging member such that it extends beyond the proximal end of the lead engaging member. The lead locking device also has a loop handle attached to the proximal end of the mandrel. The lead engaging member has a first configuration which is narrower than a second configuration and is sufficiently long to extend along substantially the entire length of a lead to be removed from a patient's body. Methods of removing a lead from a patient's body include attaching a lead locking device along substantially the entire length of the lead and applying traction to the proximal end of the lead locking device.

3 Claims, 6 Drawing Sheets

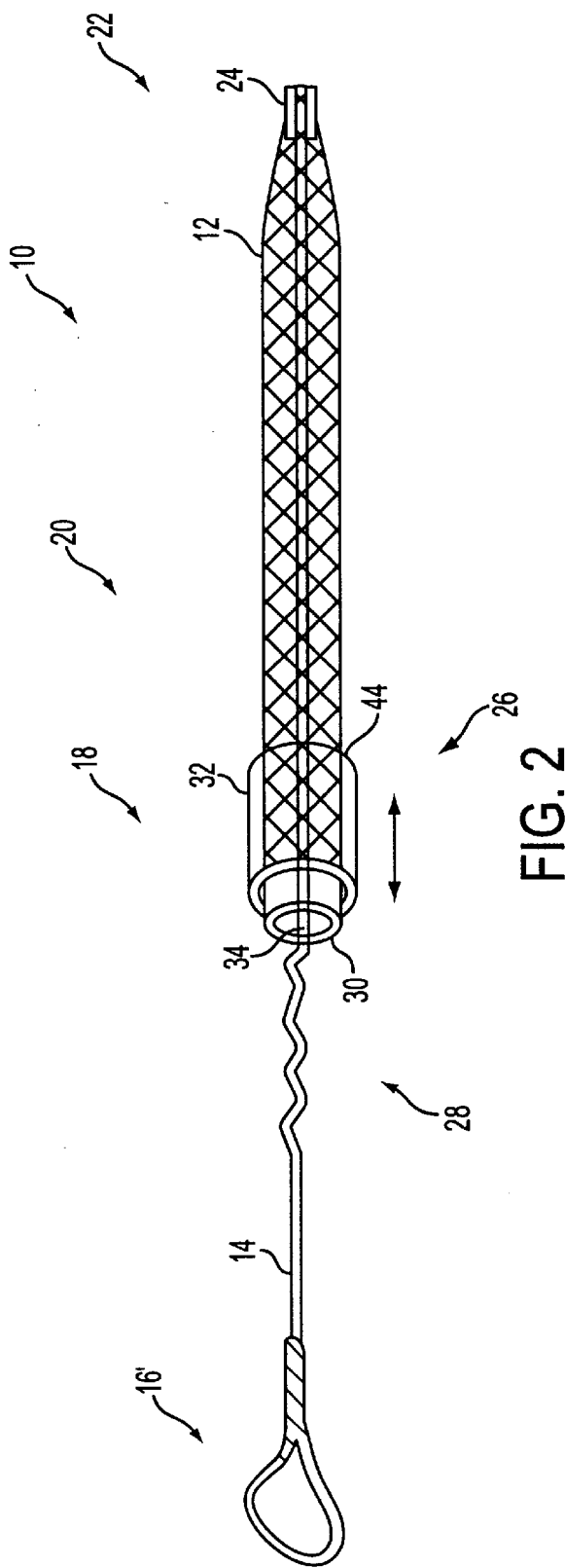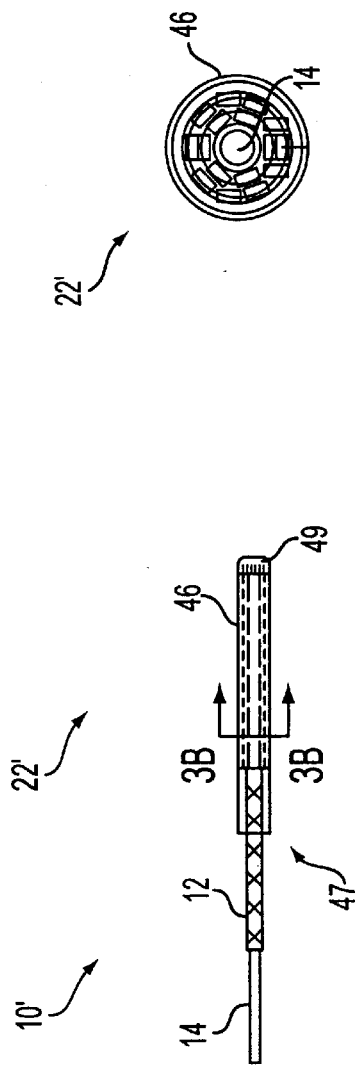

LEAD LOCKING DEVICE AND METHOD

This is a division of application Ser. No. 09/285,720, filed Apr. 5, 1999 now U.S. Pat. No 6,167,315, the entire contents of which is hereby incorporated by reference.

BACKGROUND OF THE INVENTION

1. Field of the Invention

This invention pertains to lead locking devices and methods for locking onto a lead, and more particularly to lead locking devices and methods for locking onto and removing a lead from a patient's body, such as a pacemaker lead.

2. Description of Related Art

Various medical procedures attach wire-like devices to internal portions of a person's body, such as an electrical lead for a pacemaker or a catheter. Pacemaker leads are electrically conducting wires which run to an electrode that is attached to an inner wall of a person's heart. Pacemaker leads are typically a coil of wire enclosed in an outer cylindrical sheath of electrically insulating material. The coil of wire usually leaves a hollow space running down the center of the pacing lead (a "lumen").

Pacing leads are usually implanted with the intention that they will remain in the patient for several years. During such time, fibrous tissue grows over the electrode and portions of the lead. Pacing leads are often provided with additional barb-like structures or a corkscrew type of structure to encourage adhesion to the inner wall of the patient's heart.

Pacing leads sometimes fail or it is sometimes desirable to place an electrode at a different position from a previous position. It is then necessary to determine what should be done with the unused pacing leads. Both the removal of a pacing lead and leaving it in the patient entail associated risks. Leaving the pacing lead in the patient can increase the chances of infection, interfere with the additional pacing leads, or cause additional complications. On the other hand, removing pacing leads can cause severe, and possibly fatal, damage to the patient's heart.

Numerous devices have thus been developed that can be inserted into the lumen of a pacing lead and attach to the pacing lead close to the electrode in order to apply traction to the end of the lead close to the electrode. A series of patents to Goode et al (U.S. Pat. Nos. 4,943,289; 4,988,347; 5,011,482; 5,013,310; and 5,207,683) disclose various devices which attach to the pacing lead at a localized region close to the electrode. Peers-Trevarton (U.S. Pat. No. 4,574,800), Hocherl et al (U.S. Pat. No. 5,549,615) and McCorkle (U.S. Pat. Nos. 4,471,777 and 4,582,056) disclose similar devices which attach to a pacing lead close to the electrode. However, all of these devices have a disadvantage that they attach to the pacing lead in a localized area. Applying traction to the pacing lead and/or pacing lead removing devices according to the prior art can lead to the pacing lead's becoming distorted and/or breaking before the pacing lead is successfully removed from the patient. In addition, the prior art devices rely on either a form of entanglement with the coiled wire of the pacing lead, or some form of local distortion to the coil of the pacing lead in order to maintain a firm grip with the pacing lead removing apparatus while traction is applied to the apparatus. Consequently, this makes it difficult or impossible to remove a conventional device from the pacing lead in order to abort or restart the pacing lead removing procedure.

The expandable portions of the conventional devices also make it difficult or impossible to use other lead removing equipment and procedures in conjunction with those devices. For example, a substantially cylindrical and flexible catheter which has a central lumen is often slid over the pacing lead such that the pacing lead passes through the lumen of the catheter and the leading edge of the catheter is used to free fibrous growth from the pacing lead. Laser catheters are also known to slide over a pacing lead in which laser light is transmitted along the catheter in order to cut away fibrous tissue as the laser catheter is advanced along the pacing lead. Consequently, it is also desirable to have a pacing lead removing device which can attach internally to the pacing lead so as not to obstruct a catheter or laser catheter which may be used in conjunction with the pacing lead removing device.

SUMMARY OF THE INVENTION

Accordingly, it is an object of this invention to provide a lead locking device which is insertable into a lumen of a lead and which engages and forms a grip with an extended portion of the inner region of the lead.

It is another object of this invention to provide a lead locking device which is insertable into a lumen of a lead and which engages and forms a grip with an extended portion of the inner region of the lead including at least a proximal portion.

It is another object of this invention to provide a lead locking device which is insertable into a lumen of a lead and engages the lead substantially along the entire length of the lead to form a grip with the lead.

It is another object of this invention to provide a lead locking device which is compatible for use in conjunction with a catheter threaded over the outside surface of the lead.

It is another object of this invention to provide a method of removing a pacing lead by attaching a lead locking device to an extended portion of a lead within the lumen of the lead.

It is another object of this invention to provide a method of removing a lead from a patient's body by attaching a lead locking device along substantially the entire length of a lead.

The above and related objects of this invention are realized by providing a lead locking device that has a lead engaging member extending along a longitudinal direction and defining a lumen therein. A mandrel is disposed in the lumen and attached to the distal end of the lead engaging member such that the mandrel extends substantially along the entire length of the lumen and protrudes beyond a proximal end of the lead engaging member. The lead engaging member has a first configuration in which it is slid into a lumen defined by a lead, such as a pacing lead. Preferably, the lead engaging member is sufficiently long to extend along at least about 30% of, and more preferably, substantially along the entire length of the pacing lead. When the lead engaging member extends along less than substantially the entire length of the pacing lead, it is preferable for the pacing lead to engage at least a distal portion and a proximal portion of the pacing lead; however, the scope and spirit of the invention includes generally engaging at least about 30% of the lead engaging member. The lead engaging member has a second configuration in which it engages the lead substantially along the entire length of the lumen of the lead. This engagement of the lead engaging member to the lead forms a connection or lock to the lead. By engaging the lead substantially for the entire length, the tractional force can be distributed along the lead, thus reducing distortion and breakage of a lead during the lead removal process.

The general concept of the lead engaging member engaging the pacing lead along substantially the entire length of the lead may be realized in a great variety of embodiments. In some preferred embodiments, the lead engaging member is an elastic sheath which is stretched in the first configuration and substantially relaxed in the second configuration. In a first preferred embodiment, the lead engaging member is a braided sheath of wires. Preferably, the wires are flat wires which have a rectangular cross-sectional shape. In a second preferred embodiment, the lead engaging member is a sheath of elastic material, such as rubber.

Generally, the lead engaging member has a narrower maximum diameter in the first configuration than in the second configuration. The greater diameter in the second configuration results in the lead engaging member gripping the lead from within the lumen due to frictional or other contact forces with the wall of the lumen.

The lead locking device according to the preferred embodiments has a mechanism that holds the lead engaging member in a stretched configuration. However, the general concepts of the invention are not limited to having such a mechanism to hold the lead engaging member in a stretched position. For example, the user may manually hold the lead engaging member in a stretched configuration until releasing it at a desired time. Other embodiments may provide a lead engaging member which has a larger diameter in the relaxed, lead engaging configuration and a smaller diameter in the nonrelaxed lead nonengaging configuration.

The first preferred embodiment of a mechanism that holds the lead engaging member in a stretched configuration is a press-fit mechanism. As described above, the lead locking device has a lead engaging member extending along a longitudinal direction and defining a lumen therein. The press-fit mechanism has an inner hypotube and an outer hypotube arranged concentrically to sandwich a proximal portion of the lead engaging member therebetween. A mandrel is disposed in the lumen and attached to the distal end of the lead engaging member such that the mandrel extends along at least 30% of, and more preferably substantially along the entire length of, the lumen and protrudes beyond a proximal end of the lead engaging member. A portion of the mandrel in this embodiment is crimped in a wave-like crimped pattern such that the inner and outer hypotubes, with the portion of the lead engaging member sandwiched therebetween, is slidable along the mandrel to substantially a central portion of the crimped section of the mandrel. The wave-like crimp in the mandrel supplies a resistive force to sliding the inner and outer hypotubes over it. However, the resistive force is small enough such that it can be overcome by the user operating the lead locking device. Once the inner and outer hypotubes are positioned substantially within the center of the crimped section of the mandrel, the crimped section of the mandrel supplies a resistive force which cancels the restoring force of the stretched lead engaging member. The residual resistive force of the crimped section of the mandrel is sufficiently small such that the user can slide the inner hypotube back away from the crimped section of the mandrel. The lead engaging member thus acquires a substantially relaxed configuration and increases its outer diameter which engages the surface of the lumen to provide a frictional engagement.

In other preferred embodiments, a latching mechanism holds the lead engaging member in a stretched configuration so that the surgeon does not have to manually hold the lead engaging member in the stretched configuration. The preferred embodiment of a latching mechanism is a snap-fit mechanism. The snap-fit mechanism has a first hypotube and a second hypotube arranged concentrically with a proximal portion of the lead engaging member sandwiched therebetween forming a female connector. The first hypotube has a detent extending circumferentially around the inner surface of the first hypotube. The snapfit mechanism has a male connector attached to the mandrel. The male connector has an indent along the outer surface extending in a circumferential direction. The male connector is attached to a portion of the mandrel such that when the first hypotube is pulled toward the male connector the first hypotube of the female connector engages and snaps to the male connector. The detents in the female connector fit into the indents in the male connector to hold the lead engaging member in a stretched configuration. The user slides the female connector back away from the male connector in order to unsnap the lead engaging member, thus permitting it to take on a substantially relaxed configuration.

Preferably, the lead locking device has a loop handle at the proximal end of the mandrel. The loop handle makes it easier for the user to remove the lead from the patient's body. In a preferred embodiment, the loop handle is a proximal loop made from a malleable material, and more preferably an annealed portion of the mandrel itself. A suitable material is annealed stainless steel wire. Preferably, a portion of the mandrel at the proximal end is annealed and twisted around another portion of the mandrel and encased within a proximal loop hypotube. The proximal loop hypotube is crimped to form a secure connection between the proximal handle and the mandrel. Crimping the proximal loop hypotube without adding adhesive, solder, or other material is preferred; however, the general concept of the invention is not limited to only crimping the proximal loop hypotube.

In operation, the lead locking device is inserted into a lumen of a lead such that the lead engaging member extends along at least 30% of the lead. More preferably, the lead locking device is inserted into a lumen of a lead such that the lead engaging member extends along at least 30% of the lead so that it includes a proximal and a distal portion of the lead. Even more preferably, the lead engaging member is inserted into a lumen of a lead such that the lead engaging member extends along substantially the entire length of the lead.

The lead engaging member is in a stretched configuration while it is being inserted into the lumen of the lead so that it has a smaller diameter than that of the lumen. Once the lead engaging member is fully inserted into the lumen of the lead, the surgeon releases a lead engaging member, or disengages the mechanism holding the lead engaging member in the stretched configuration, such that the lead engaging member acquires a substantially relaxed configuration. The lead engaging member thus acquires a larger outer diameter than it had in the stretched configuration. In the substantially relaxed configuration, the lead engaging member engages the lead, thus forming a connection along at least about 30% of the lead, and more preferably substantially along the entire length of the lead, due to its increased outer diameter. The surgeon applies traction to the proximal end of the lead locking device, preferably using the loop handle. The loop handle also provides greater control over the lead locking device for the removal of the lead from the patient's body. The lead locking device may be selectively removed from the lead, either before or after removing the lead from the patient's body, by restretching the lead engaging member such that it is again in a stretched configuration. After reacquiring the stretched configuration, the lead locking device disengages from and becomes unlocked from the lead since it again has a smaller outer diameter than the lumen diameter. Insertion and removal of the lead locking device from the lead may include twisting as well as pushing and pulling action from the user. Furthermore, removing the lead from the patient's body may also include twisting action, preferably using the loop handle, as well as applying traction, pulling, or pushing actions.

In a third preferred embodiment of the lead locking device, the lead engaging member is a coil attached to the distal end of a mandrel that extends along at least about 30% of, and more preferably substantially along the entire length of, the entire length of a lead. The lead locking device according to the third embodiment has a tightly wound configuration for the lead engaging member, such that it has a smaller outer diameter than the diameter of the lumen. The lead locking device is inserted into the lumen of the lead while the coil of the lead engaging member is in the tightly wound configuration such that the coil extends substantially along the entire length of the lead within the lumen of the lead. The surgeon rotates the mandrel relative to the proximal end of the coil in order to partially unwind the coil such that it takes on a loosely wound configuration which has an increased outer diameter as compared to the tightly wound configuration. The coil in the loosely wound configuration has a greater diameter than in the tightly wound configuration, it thereby engages and locks onto the lead from within the lumen of the lead. The surgeon applies traction to the proximal end of the mandrel in order to remove the lead from the patient's body.

In a fourth preferred embodiment, the lead engaging member is a helical ribbon wrapped around a mandrel in which the distal end of the ribbon and the distal end of the mandrel are attached, preferably by adhesive material. The helical ribbon of the lead engaging member is nonoverlapping in a first configuration. The surgeon inserts the lead locking device into the lumen of the lead while the ribbon of the lead engaging member is in the nonoverlapping configuration such that the ribbon extends along at least 30% of, and more preferably substantially along the entire length of, the lead. Once the lead locking device is fully inserted into the lumen of the lead, the surgeon applies traction to the mandrel causing the helical ribbon of the lead engaging member to partially overlap itself, thus resulting in an increase in diameter of the lead engaging member. The increase in diameter of the lead engaging member forms a contact along at least 30% of, and more preferably substantially along the entire length of, the lumen of the lead.

BRIEF DESCRIPTION OF THE DRAWINGS

These and other objects and advantages of the invention will become more apparent and more readily appreciated from the following detailed description of the presently preferred exemplary embodiments of the invention, taken in conjunction with the accompanying drawings, of which:

FIG. 2 is a schematic illustration of the lead locking device according to the first embodiment of the invention;

FIG. 3A is a blown-up view of a section of FIG. 1;

FIG. 3B is a cross-sectional view of the portion of the lead locking device illustrated in FIG. 3A;

DETAILED DESCRIPTION OF THE PREFERRED EMBODIMENT

Figure 1:
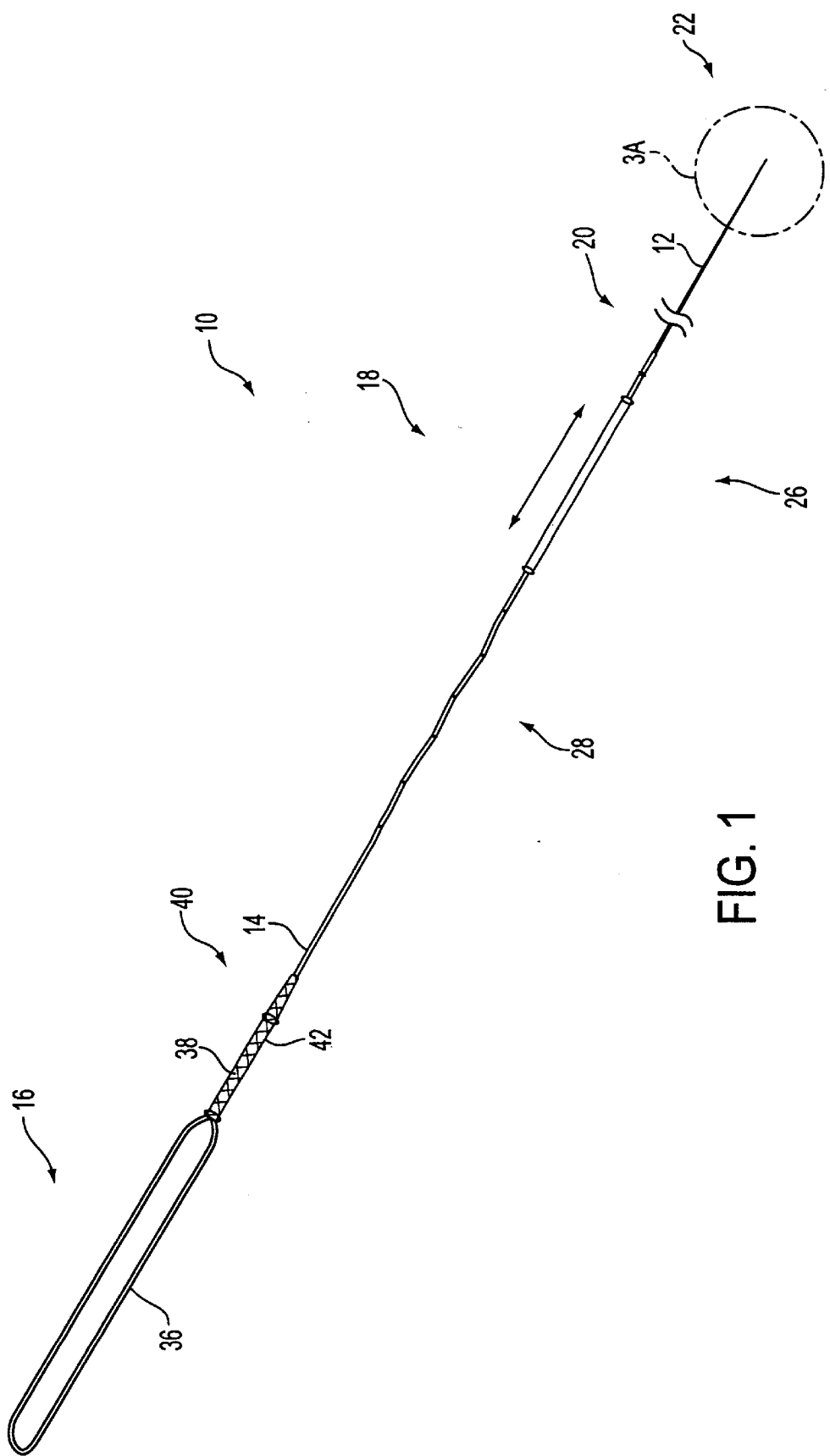
FIG. 1 illustrates a lead locking device according to the first embodiment of the invention.

Reference numeral 10 in FIG. 1 generally represents a lead locking device according to a first embodiment of the invention. The lead locking device 10 has a lead engaging member 12, a mandrel 14, a loop handle 16 and a press-fit type of latching mechanism 18. The lead engaging member 12 has a proximal end 20 and a distal end 22. FIG. 1 shows a section of the lead engaging member 12, between the proximal end 20 and the distal end 22, with the center portion cut away for illustration purposes. Consequently, FIG. 1 does not illustrate the scaled length of the lead engaging member 12. Preferably, the lead engaging member 12 is at least about 65 cm long. However, the length of the lead engaging member 12 may be selected according to the intended application. As one may see illustrated schematically in FIG. 2, the lead engaging member 12 defines a lumen extending between the proximal end 20 and distal end 22. The mandrel 14 is disposed in the lumen defined by the lead engaging member 12 and attached to the distal tip 24 of the lead engaging member 12. In a preferred embodiment, the lead engaging member 12 is a braided sheath. The lead engaging member 12 is soldered to the mandrel 14 at the distal tip 24 in a first embodiment. The solder at the distal tip 24 is preferably a radiopaque solder. Suitable materials for the radiopaque solder are alloys of gold and tin. More preferably, the solder at the distal tip 24 is about 80% gold and about 20% tin.

In a preferred embodiment, the press-fit type of latching mechanism 18 has at least a portion 26 attached to the proximal end 20 of the lead engaging member 12 and a crimped portion 28 of the mandrel 14. Preferably, the portion of the press-fit mechanism 26 attached to the proximal end 20 of the lead engaging member 12 has an inner hypotube 30 and an outer hypotube 32 concentrically arranged to sandwich the proximal end 20 of the lead engaging member 12 therebetween. Preferably, the inner hypotube 30 and outer hypotube 32 are crimped to become mechanically fixed to the lead engaging member 12. The inner hypotube 30 and outer hypotube 32, which are preferably rigidly fixed with respect to each other and to a proximal end 20 of the lead engaging member 12, is slidable along the mandrel 14 disposed in the lumen defined by the lead engaging member 12. The crimped section 28 in the mandrel 14 is constructed at a position relative to the proximal end 20 of the lead engaging member 12 such that the inner hypotube 30 and outer hypotube 32 attached to the proximal end 20 of the lead engaging member 12 overlaps the crimped section 28 of the mandrel 14 when the lead engaging member 12 is in a stretched configuration. More preferably, the inner hypotube 30 and outer hypotube 32 attached to the proximal end 20 of the lead engaging member 12 sets in a stable condition, thus being held or "latched" in place, approximately in the center of the crimped section 28 when the lead engaging member 12 is in a stretched configuration. In the preferred embodiment, the inner hypotube 30 and outer hypotube 32 attached to the roximal end 20 of the lead engaging member 12 is beyond the most distal end 4 in the distal direction when the lead engaging member 12 is in a ubstantially relaxed configuration.

As one may see illustrated in FIG. 1, the loop handle 16 of the lead locking device 10 preferably has a proximal loop 36 and an end portion 38 which is further twisted around the most proximal end 40 of the mandrel 14. In the preferred embodiment, a proximal loop hypotube 42 is disposed over the twisted end 38 of the loop handle 16 and crimped to mechanically attach the loop handle 16 to the mandrel 14. Preferably, the proximal loop hypotube 42 is crimped, thereby forming a solid mechanical attachment of the loop handle 16 to the mandrel 14.

Preferably, the proximal loop 36 is made from annealed stainless steel wire, thus providing a degree of malleability. More preferably, the stainless steel wire of the proximal loop 36 is an annealed portion of the most proximal end of the mandrel 14 itself. Stainless steel 304V wire about 0.020" thick with about 20 cm annealed at the proximal end has been found to be suitable for the mandrel 14 with a proximal loop 36. Preferably, the proximal loop hypotube 42 is 304V stainless steel.

In the preferred embodiment, the mandrel 14, the inner hypotube 30 and the outer hypotube 32 are 304V stainless steel. In the first preferred embodiment, the lead engaging member 12 is a braided sheath. Preferably, the lead engaging member 12 is a braided sheath of flat wires which have a rectangular cross-section. Preferably, the flat wires of the braided sheath of the lead engaging member 12 are 304V stainless steel. More preferably, the flat wires have cross-sectional dimensions of about 0.001×0.003". A braided sheath for the lead engaging member 12 formed from about 16 flat wires was found to be suitable for specific applications. In addition, an outer diameter of the lead engaging member 12 of 0.016" in the stretched configuration and about 0.045" in a substantially relaxed configuration were found to be suitable for specific applications. Preferably, the tip of the lead locking device is less than about 0.017 inch. In a preferred embodiment, the mandrel 14 tapers from the proximal end to the distal end. Thicknesses of the mandrel 14 ranging from about 0.020" to about 0.011" going from the proximal end to the distal end were found to be suitable for particular applications. The lead locking device 10 may also include a fillet provided at the interface between the outer hypotube 32 and the lead engaging member 12, although it is currently more preferred not to include a fillet. A suitable material for the fillet, if included, is glue or solder.

As one may see in another preferred embodiment illustrated in FIGS. 3A and 3B, the lead locking device 10' includes a distal band 46 attached to the distal end 22'. FIG. 3A is an enlarged view of a section of the lead locking device 10', except the distal end 46 replaces the solder tip 24 illustrated in FIG. 2. The distal band 46 is disposed over a distal portion 48 of the lead engaging member 12. Preferably, the distal band 46 and the distal portion 48 are joined together. The distal band 46 and distal portion 48 of the lead engaging member 12 are preferably joined together by epoxy disposed therebetween. The epoxy permeates the braid of the distal portion 48 of the lead engaging member 12 up to a wick length 47. More preferably, an epoxy plug 49 is formed at the distal end of the lead locking device 10', mechanically locking the distal band 46 to the lead engaging member 12 and mandrel 14. The epoxy plug reduces fraying of the wires forming the braided lead engaging member if one, or some, of the wires break. In other embodiments, it is also suitable to join the distal band 46 and the distal portion 48 by other adhesives, soldering, welding or by crimping. A suitable material for the distal band is an alloy of platinum and iridium (preferably 90% Pt and 10% Ir).

Figure 4:
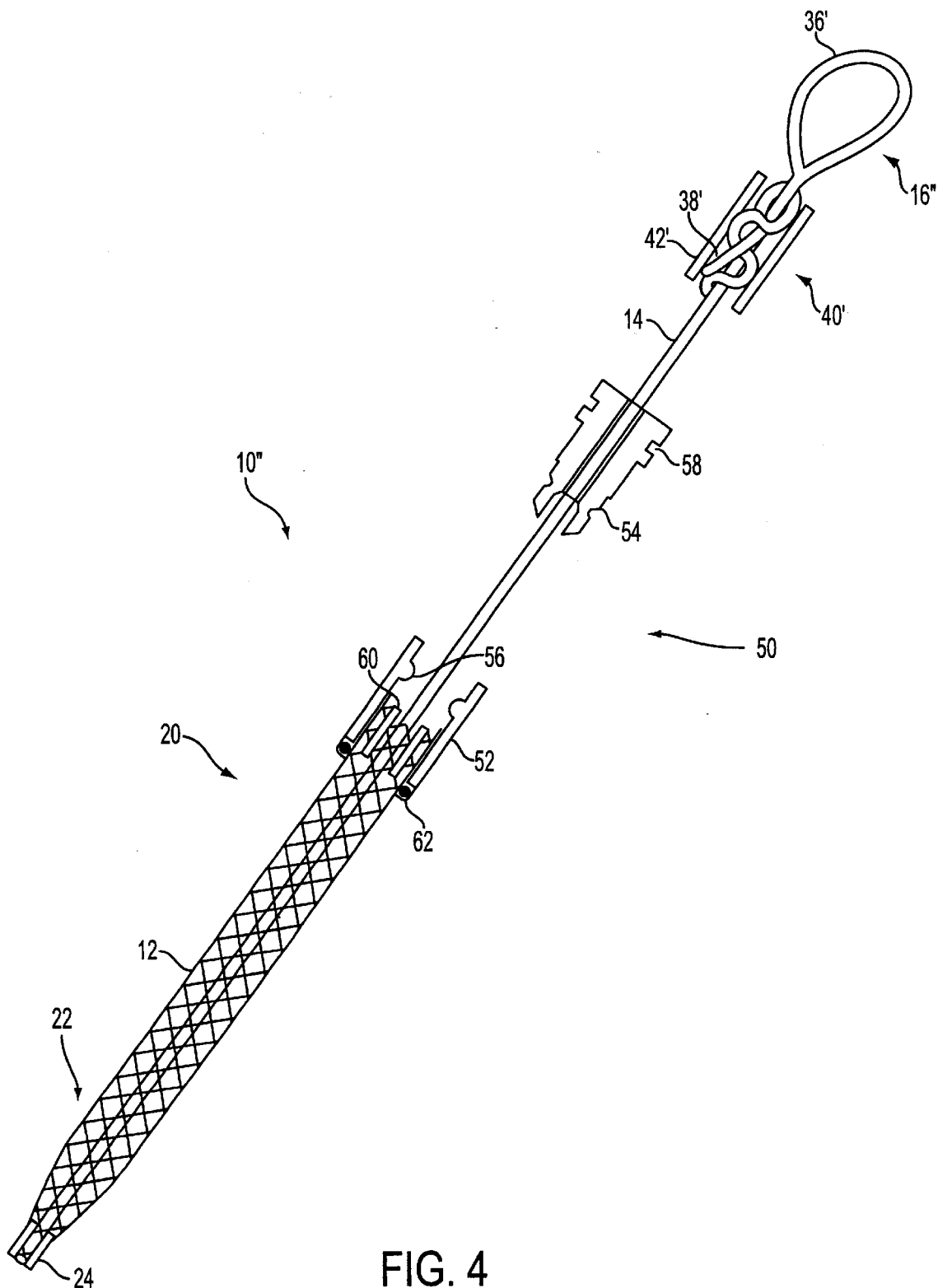
FIG. 4 is a schematic illustration of a lead locking device which has a second embodiment of a mechanism to hold the lead engaging member in a stretched configuration.
Figure 4A:
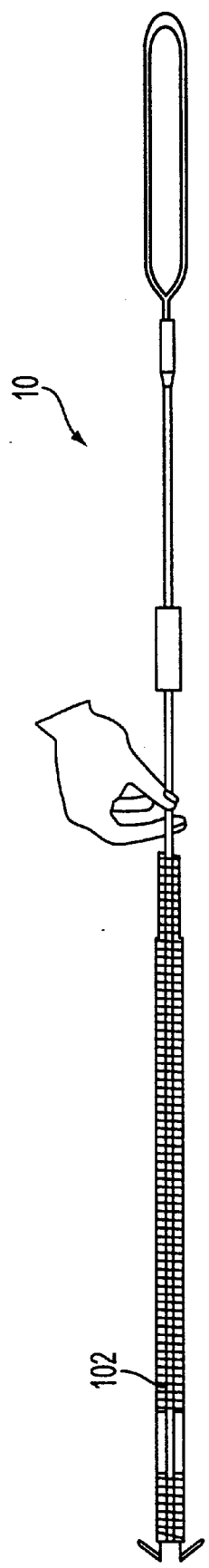
FIG. 4A is a schematic illustration of the head locking device according to FIG. 1 and a peacemaker lead.

FIG. 4 is a schematic illustration of a lead locking device 10" which is similar to the lead locking device 10, but it has a latching mechanism 50 instead of a press-fit type of latching mechanism 18. In the lead locking device 10", the loop handle 16" is similar to the loop handle 16. The loop handle 16" forms a proximal loop 36' an end 38' that is twisted around another portion of the mandrel 14. A proximal loop hypotube 42' is preferably disposed over the twisted end 38' of the loop handle 16" which is crimped. In the preferred embodiment of the lead locking device 10" the latching mechanism 50 has a portion 52 attached to the proximal end of the lead engaging member 12. Preferably, the latching mechanism 50 also has a portion 54 attached to a proximal portion of the mandrel 14 that provides a male connector. The portion 52 attached to the proximal end 20 of the lead engaging member 12 is selectively and removably attachable to the portion 54 attached to the proximal end of the mandrel 14. More preferably, the portion 52 attached to the proximal end 20 of the lead engaging member 12 and the portion 54 attached to the proximal portion of the mandrel 14 cooperatively form a snap-fit latching mechanism. More preferably, the portion 52 attached to the proximal end 20 of the lead engaging member 12 is a first hypotube having a detent 56 defined by an inner surface of the first hypotube 52. Preferably, the portion 54 attached to a proximal portion of the mandrel 14 has an outer surface that defines an indent 58. The detent 56 is secured within the indent 58 in a latched configuration of the latching mechanism 50, thus holding the lead engaging member in a stretched configuration. In the preferred embodiment, a second hypotube 60 is slidably disposed over the mandrel 14 and arranged concentrically with the first hypotube 52 such that a proximal portion 20 of the lead engaging member 12 is disposed therebetween. The concentric arrangement of second hypotube 60, the proximal portion 20 of the lead engaging member 12 and the first hypotube 52 are securely attached by at least one of adhesive material, welding and crimping, but preferably by crimping, to form a female connector. Although the lead locking device 10" has a distal tip 24 as in the lead locking device 10, a distal band such as in the lead locking device 10' may also be used in this embodiment. The material of the first and second hypotubes 52 and 60 is preferably stainless steel. The material of the portion 54 is preferably stainless steel or a polymer. A fillet may also be provided at the interface of the first hypotube 52 and the proximal end 20 of the lead engaging member 12. The fillet, if used, is preferably glue or solder.

In operation of the lead locking device 10, the user slides the portion 26 of the press-fit type of latching mechanism 18 that is attached to the proximal end 20 of the lead engaging member 12 along the mandrel 14 in a direction from the distal tip 24 towards the loop handle 16 until the inner hypotube 30 and outer hypotube 32 are positioned approximately at the center of the crimp 28. The crimped portion 28 of the mandrel 14 provides resistance to sliding the inner hypotube 30 and outer hypotube 32 thereon. Similarly, once the inner hypotube 30 and outer hypotube 32 are positioned over the crimped portion 28 of the mandrel 14, the crimped portion of the mandrel 14 provides a resistive force which cancels the restoring force provided by the lead engaging member 12 in the stretched configuration, thus holding it in place.

The lead engaging member 12 is disposed in a lumen defined by a lead, for example, a pacing lead for a pacemaker. Pacing leads are coiled, thus forming a lumen therein. The lead engaging member 12 is inserted into the lead lumen until it is disposed along at least about 30% of the length of the pacing lead, and more preferably substantially along the entire length of the pacing lead. The surgeon, or other user of the lead locking device 10, releases the press-fit type of latch mechanism by sliding the inner hypotube 30 and outer hypotube 32 combined unit toward the distal tip 24. The additional force provided by the surgeon overcomes the resistive force provided by the crimped portion 28 of the mandrel 14. The lead engaging member 12 thus acquires a substantially relaxed configuration such that it has a larger diameter than when it was in a stretched configuration. The wider diameter of the lead engaging member 12 acts to frictionally engage and lock the lead engaging member 12 to an inner surface of the lumen of the lead, along at least about 30%, and more preferably substantially the entire length of the lead. Flat braided wires in the lead engaging member 12 enhance the quality of the grip between the lead engaging member 12 and the inner portions of the lead. Furthermore, the flexibility of the lead engaging member 12 compensates for variations in the shape and size of the lumen of the lead to ensure a good grip along an extended portion of the lumen.

Traction is then applied to the mandrel 14, which may be primarily provided by applying traction to the loop handle 16. Since the lead locking device 10 is locked along at least about 30%, and more preferably substantially the entire length of the lead, the traction is distributed over an extended portion of the lead rather than being applied in a small local region. In addition, by engaging the lead along at least about 30% of the lumen of the lead to include at least a proximal portion and at least a distal portion of the lead, traction forces are distributed to at least a proximal portion and a distal portion of the lead. By distributing the traction force over an extended portion of the lead, distortions, disruptions and breakage of the lead are reduced.

The lead locking device 10 may also be unlocked, and removed, from the lead prior to removing the lead from the patient's body. This may be done to abort the operation, remove and reconfigure the lead locking device 10, remove the lead locking device 10 and replace it with another device, or to remove the lead locking device to apply other methods and techniques. To release the lead locking device from the lead, the surgeon slides the inner hypotube 30 and outer hypotube 32 arrangement towards the proximal end, away from the distal tip 24, thus restretching the lead engaging member 12.

In the preferred embodiment, the flat wires of the braided sheath of the lead engaging member 12 lock along an extended length of the lead. The lead locking devices 10' and 10" operate in a manner similar to that of lead locking device 10. After inserting the lead locking device 10" into the lumen of a lead, the surgeon applies traction to the mandrel 14, which may be primarily applied through the loop handle 16". The lead locking device 10" may be removed from the lead either before or after removal of the lead from the patient's body by sliding the first hypotube 52 away from the distal tip 24 towards the loop handle 16" such that the first hypotube 52 forms a snap-fit with the portion 54 attached to the mandrel 14. Once the detente 56 is secured within the indent 58, the lead engaging member 12 is held in a stretched configuration, thus having a narrower outer diameter than in the relaxed configuration. The surgeon then applies traction to the lead locking device 10" through the mandrel 14 to remove the lead locking device 10" from the lead. Although the preferred embodiment of the lead locking device 10 has a press-fit mechanism, and the lead locking device 10" has a snap-fit mechanism, the general concepts of the invention are not limited to prestretching the lead engaging member in only these ways. One skilled in the art would recognize, based on the above teachings, that numerous other mechanisms may be used.

Figure 5A:
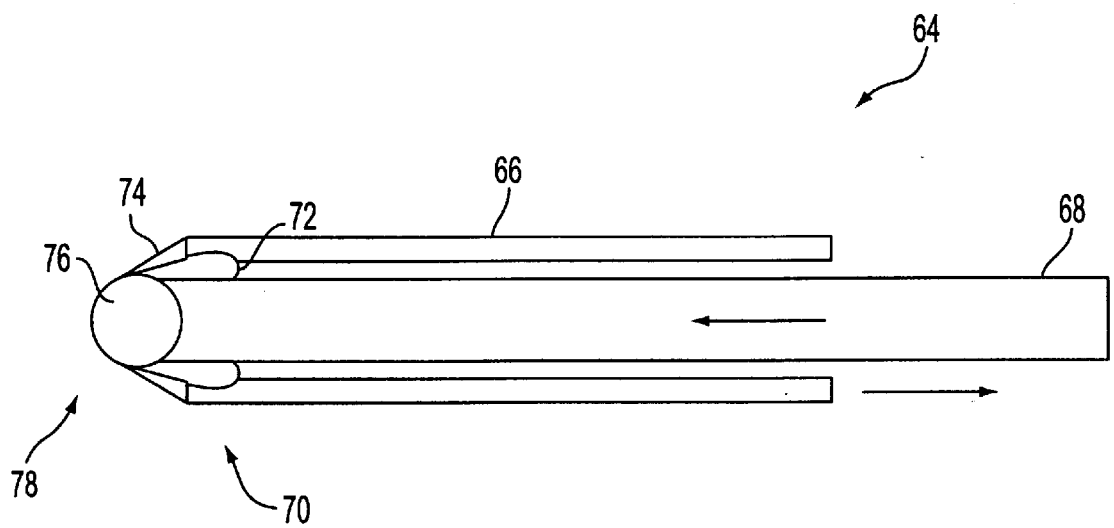
FIG. 5A and FIG. 5B illustrate two configurations of a second embodiment of the lead locking device according to the invention.
Figure 5B:
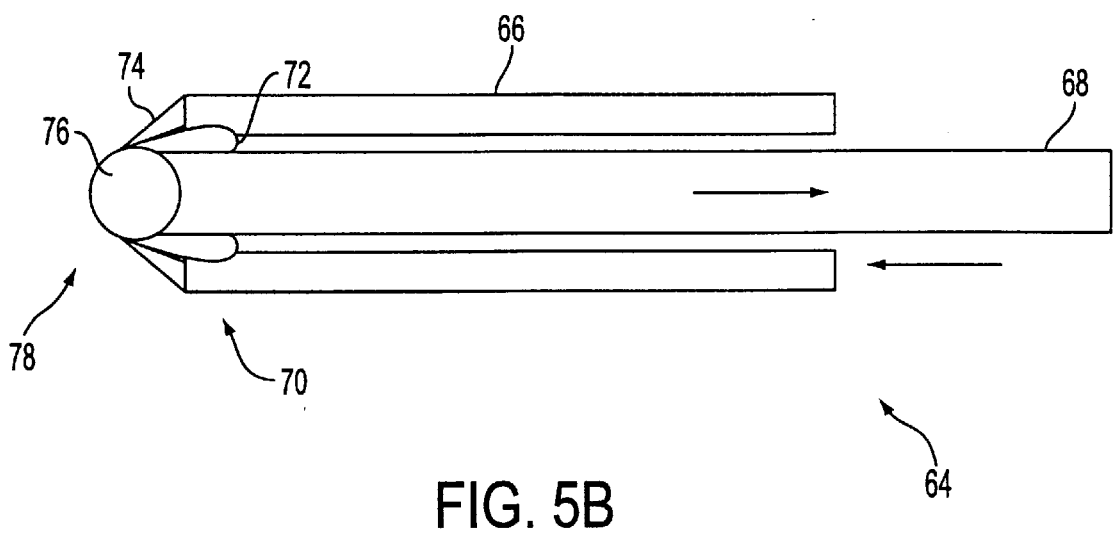

FIGS. 5A and 5B show a second preferred embodiment of the invention. The lead locking device 64 has a lead engaging member 66 and a mandrel 68. The mandrel 68 is disposed in a lumen defined by the lead engaging member 66 and attached at the distal end 70 of the lead engaging member 66. The lead engaging member 66 is preferably attached to the mandrel 68 by adhesive material 72. A fillet 74 is attached at an interface between the lead engaging member 66 and the distal end 70 of the mandrel to form a smoother fit. In addition, a spherical element 76 may be attached to the distal tip 78 of the lead locking device 64 in order to form a smooth and rounded tip. In the second preferred embodiment, the lead engaging member 66 is an elastic material such as a rubber material. FIG. 5A shows the lead engaging member in a stretched configuration. The lead locking device 64 may also employ a press-fit or latching mechanism as in the lead locking devices 10 and 10", or may be used without such a mechanism in which case the surgeon holds the lead locking member 66 in a stretched configuration. Similarly, the lead locking devices 10 and 10" may also be used without the press-fit and latching mechanisms, in which case the surgeon may hold the braided lead locking member in a stretched configuration and release it for it to acquire a substantially relaxed configuration.

FIG. 5B shows the lead engaging member 66 in a substantially relaxed configuration in which it has a greater outer diameter than in the stretched configuration, as illustrated in FIG. 5A.

The lead locking device 64 is used in a similar manner to the lead locking devices 10, 10', and 10". The surgeon stretches the lead engaging member 66, inserts the lead engaging member 66 into a lumen defined by a lead, and releases the lead engaging member 66 such that it takes on a substantially relaxed configuration. The lead engaging member 66 in the stretched configuration has a narrower outer diameter than the diameter of the lumen. Upon releasing the lead engaging member 66 it engages the lead lumen and locks onto the lead, along at least 30%, and more preferably along the entire length of the lead since it has a diameter substantially equal to or greater than the lumen diameter in the relaxed configuration. The surgeon then applies traction to the mandrel 68 which may include an attached loop handle. The lead locking device 64 is similarly removable from the lead, either before or after the lead is removed from the patient's body.

Figure 6:
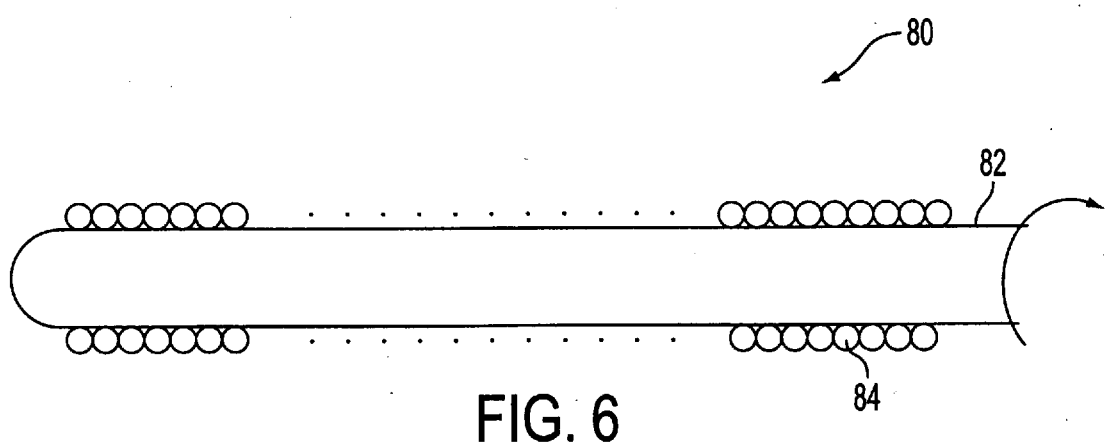
FIG. 6 illustrates a third embodiment of a lead locking device according to the invention.

FIG. 6 is an illustration of the third embodiment of the invention. The lead locking device 80, according to the third embodiment has a mandrel 82 with a coil 84 wrapped therearound. The coil 84 is preferably metal wire. More preferably, the coil 84 is stainless steel wire. The lead locking device 80 has a tightly wrapped configuration with an outer diameter less than the lumen diameter when it is inserted into the lumen defined by a lead. After the surgeon inserts the lead locking device 80 such that the coil 84 extends substantially along the entire length of the lead, the surgeon rotates the mandrel 82 about a longitudinal axis so as to cause the coil 84 to partially unwind, thus obtaining a loosely wound configuration with an increased diameter. The coil 84 in the loosely wound configuration locks onto the lead along at least about 30%, and more preferably along substantially the entire length of the lead by friction or other contact forces. The surgeon then applies traction to the mandrel 82 to remove the lead from the patient's body. The lead locking device 80 can be removed from the lead either before or after the lead is removed from the patient's body by rotating the mandrel in a direction to cause the coil 84 to wind more tightly, thus obtaining a tightly wound configuration. The surgeon then can remove the lead locking device 80 from the lead by applying traction to the mandrel 82 without significant traction being applied to the lead.

Figure 7A:
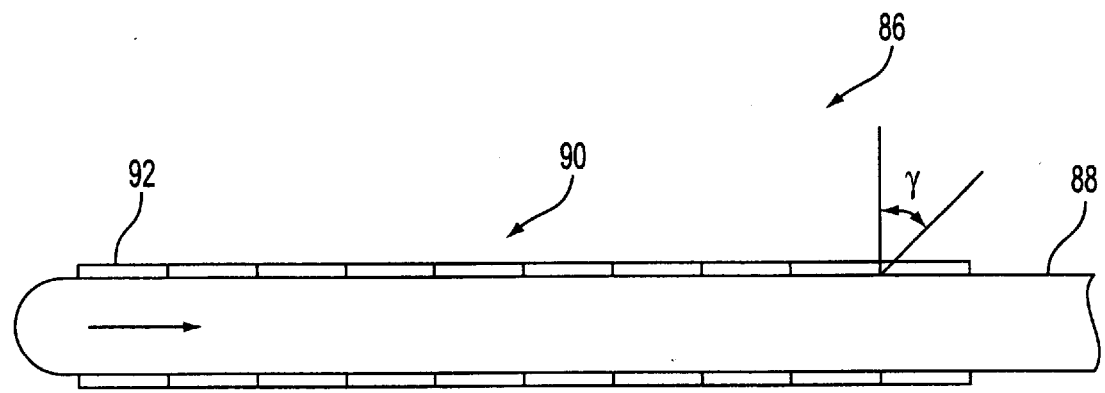
FIG. 7A and FIG. 7B illustrate two configurations of a lead locking device according to a fourth embodiment of the invention.
Figure 7B:
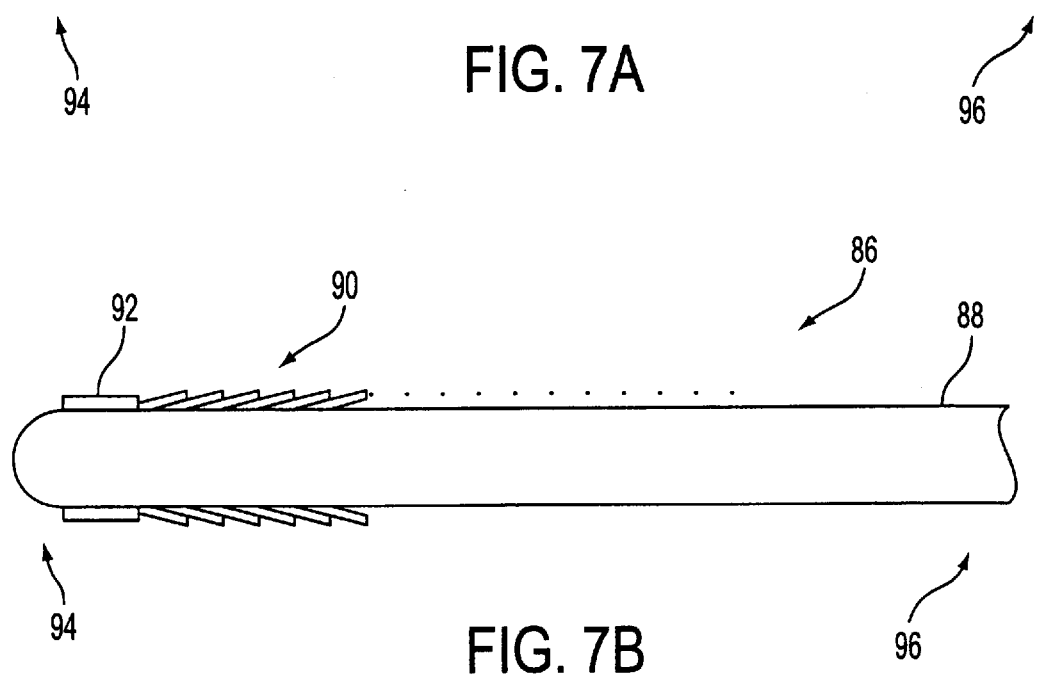

FIGS. 7A and 7B show a fourth embodiment of a lead locking device according to the invention. The lead locking device 86 according to the fourth embodiment has a mandrel 88 and a helical ribbon 90 wrapped around the mandrel 88. The most distal portion 92 of the helical ribbon 90 is attached to the mandrel 88, preferably by adhesive or welding. The interface between adjacent portions of the helical ribbon 90 preferably has an up-slope from the distal end 94 to the proximal end 96 of the mandrel which is an acute angle γ. Preferably, the angle between all adjacent portions of the ribbon meet at a substantially uniform angle γ. In operation, the surgeon inserts the lead locking device 86 into a lumen defined by a lead until the helical ribbon 90 extends along at least about 30%, and more preferably substantially along the entire lead. The surgeon applies traction to the mandrel 88 which causes the helical ribbon 90 to partially overlap itself, as illustrated in FIG. 7B. The outer diameter of the lead engaging member 90 in the configuration illustrated in FIG. 7B is larger than that illustrated in FIG. 7A. Consequently, the lead engaging member 90 locks onto the lead along at least 30%, and more preferably substantially along the entire length of the lead.

The surgeon can remove the lead locking device 86 from the lead, either before or after removing the lead from the patient's body. In order to remove the lead locking device 86 from the lead, the surgeon pushes on the mandrel 82 towards the distal tip 94. The lead engaging member 90 then reacquires the configuration illustrated in FIG. 7A, which permits the surgeon to apply traction on the lead 88 to remove it from the lead without it transferring significant traction to the lead.

Each of the lead locking devices according to the third embodiment 80 and the fourth embodiment 86 may also have a press-fit or a latch mechanism and may have a loop handle as in the first and second embodiments.

One skilled in the art would recognize from the teachings of the specification that one may provide other configurations which include pliable material or expandable and contractible lead engaging members without departing from the general scope and spirit of the invention. Furthermore, one skilled in the art would recognize from the above teachings that many modifications and variations are possible without departing from the scope and spirit of the invention.

We claim:

1. A method of removing a lead implanted in a patient's body, comprising:

inserting a lead locking device into a lumen defined by said lead, said lead locking device comprising an elastic lead engaging member that extends along substantially the entire length of said lead, said elastic lead engaging member having a narrower radial dimension in a longitudinally stretched configuration than in a relaxed configuration, wherein said elastic lead engaging member is in said longitudinally stretched configuration during said inserting said lead locking device;

releasing said elastic lead engaging member of said lead locking device, wherein said elastic lead engaging member returns to a substantially relaxed configuration after being released, said elastic lead engaging member having a relaxed radial dimension that is substantially equal to an inner diameter of said lumen of said lead; and applying traction to said lead locking device, wherein said elastic lead engaging member engages said lead along substantially the entire longitudinal length of said lead.

2. A method of removing a lead implanted in a patient's body according to claim 1, further comprising:

longitudinally stretching said elastic lead engaging member prior to removing said lead from said patient's body; and removing said lead locking device from said lumen of said lead.

3. A method of removing a lead implanted in a patient's body according to claim 2, further comprising:

reinserting said lead locking device back into said lumen defined by said lead;

releasing said elastic lead engaging member of said lead locking device after said reinserting said lead locking device; and applying traction to said lead locking device.

\* \* \* \* \*